United States Patent [19]

Monroy

[11] 3,940,451

[45] Feb. 24, 1976

[54] PROCESS OF RECOVERING BHT VALUES FROM MOTHER LIQUORS OF THE CRYSTALLIZATION OF BHT OBTAINED BY ALKYLATING P-CRESOL WITH ISOBUTYLENE

[76] Inventor: Heliodoro Monroy, Insurgentes Sur 591-7th Floor, Mexico City, Mexico

[22] Filed: Sept. 6, 1974

[21] Appl. No.: 503,569

[52] U.S. Cl...... 260/624 A; 260/621 A; 260/621 H; 260/627 G
[51] Int. Cl.$^2$............................................ C07C 39/06
[58] Field of Search........ 260/627 G, 624 A, 624 R, 260/621 L, 621 D, 621 H, 621 A

[56] References Cited
UNITED STATES PATENTS

| | | | |
|---|---|---|---|
| 2,366,497 | 1/1945 | Dawson | 260/621 D |
| 2,428,745 | 10/1947 | Stillson | 260/624 R |
| 2,498,999 | 2/1950 | Offutt | 260/683 |
| 2,553,538 | 5/1951 | Arnold | 260/621 D |
| 2,733,274 | 1/1956 | Cowie | 260/624 |

*Primary Examiner*—James O. Thomas, Jr.
*Assistant Examiner*—W. B. Lone
*Attorney, Agent, or Firm*—Sughrue, Rothwell, Mion, Zinn & Macpeak

[57] ABSTRACT

A process of recovering BHT values from the mother liquors of the crystallization of BHT obtained by alkylating p-cresol with isobutylene in the presence of a catalyst and crystallizing the BHT, comprises thermally cracking the starting mother liquor at a temperature of from 200°C to 250°C in the presence of an acid catalyst to reform the cresol polymers, steam distilling the cracked mixture to increase the p-cresol content and remove the diisobutylene, realkylating the steam-distilled reaction mixture with additional isobutylene, to produce a crystallizable mixture of BHT having a BHT concentration of from 80 to 85% by weight, and recovering the BHT by crystallization.

The mother liquors remaining after realkylation and crystallization can be admixed with the starting mother liquors and reused in the thermal cracking step of the process.

8 Claims, No Drawings

PROCESS OF RECOVERING BHT VALUES FROM MOTHER LIQUORS OF THE CRYSTALLIZATION OF BHT OBTAINED BY ALKYLATING P-CRESOL WITH ISOBUTYLENE

BACKGROUND OF THE INVENTION

The present invention refers to processes of recovering BHT values from the mother liquors of the crystallization of BHT obtained by alkylating p-cresol with isobutylene and, more particularly, it is related to a novel process of recovering said BHT values from mother liquors which contain relatively high concentrations of crystallization inhibiting compounds such as diisobutylene and lower and higher polymers of cresol preventing further crystallization of BHT.

In the past is has been very well known that 2,6-di-tert-butyl-p-cresol, also known as butylated hydroxy toluene or BHT, can be easily obtained by alkylation of p-cresol with isobutylene in the presence of a suitable acid catalyst such as sulfuric acid or phosphoric acid. This process for producing BHT, however, comprises as the last step a crystallization operation in order to remove the 2,6-di-tert-butyl-p-cresol from the reacted mixture obtained by the alkylation reaction with normal yields of BHT of from 75 to 80% of the theoretically possible obtention of BHT from the starting materials.

The mother liquors of the BHT crystallization step generally contain high proportions of diisobutylene and lower and higher polymers of cresol, together with realkylatable material consisting of residual p-cresol and monobutylated hydroxy toluene (tert-butyl-p-cresol) whereby it has been thought that realkylation of these BHT values could be effected to form additional BHT and thereby increase the amount already contained in said mother liquors to be furtherly crystallized. However, it has been shown that, while realkylation of the monoalkylated hydroxy toluene and of the residual p-cresol contained in the mother liquors can be easily effected by the very well known catalytic alkylation reaction described above, it is practically impossible to crystallize the thus obtained BHT from the resulting realkylated mixture, in view of the fact that apparently the presence of large proportions of diisobutylene and of lower and higher polymers of cresol, act as crystallization inhibiting compounds which prevent said crystallization.

In view of the above, regardless of the fact that the BHT values extant in the mother liquors of crystallization of the BHT-process clearly indicate that realkylation of said mother liquors could be effected in order to recover said BHT values, the existence of said crystallization inhibiting compounds (diisobutylene and cresol polymers) has prevented hereinbefore the use of these mother liquors in order to recover the BHT values contained therein, thus forcing the manufacturers to consider these mother liquors as waste materials which should be disposed of at a relatively high cost.

In view of the above, a process for the removal of the diisobutylene and lower and higher polymers of cresol from mother liquors obtained from the crystallization of BHT from the reacted mixture of p-cresol and isobutylene has been for long sought, which could economically remove said objectionable materials and thus provide a mother liquor which could be realkylated to recover the BHT values contained therein in large proportions.

Serious attempts have been made in the past to try to remove these objectionable crystallization inhibiting materials from the mother liquors of the BHT-process, without any success, inasmuch as all said processes relied mainly on the fractional distillation of the materials, which is a rather expensive procedure and does not provide for the proper reduction of the lower and higher polymers of cresol, regardless of the fact that said distillation process indeed reduces the contents of diisobutylene in the mother liquors. In other words, a vacuum distillation process of the mother liquors generally considerably reduces the content of the objectionable diisobutylene, but has the undesirable side effect of furtherly polymerizing the existing cresol and the monobutylated hydroxy toluene, forming additional amounts of lower cresol polymers and also has the objectionable side effect of furtherly polymerizing the lower polymers of cresol to produce certain amounts of higher polymers of cresol which are still more objectionable as to the properties of the mixture to permit efficient crystallization of the BHT which may be produced by realkylation of the BHT values contained therein.

The vacuum distillation procedures used heretofore, therefore, have not been successful, and certain other attempts involving reactions with proper reactants to precipitate the polymers of cresol have also been unsuccessful, thereby rendering said processes unuseful in industry, whereby the said mother liquors of the BHT-process have remained as waste materials without possibility of any further use for the recovery of the BHT values contained therein.

BRIEF SUMMARY OF THE INVENTION

Having in mind the defects of the prior art procedures for recovering BHT values from mother liquors of recrystallization of BHT, it is an object of the present invention to provide a highly economical and efficient process for the recovery of such BHT values from mother liquors of crystallization of the BHT process, which will solve all the problems of the prior art processes.

Another object of the present invention is to provide a process for the recovery of BHT values, of the above described character, which will considerably and economically reduce the concentrations of diisobutylene and cresol polymers from said mother liquor, thus permitting proper crystallization of the BHT obtained by realkylation thereof.

Still another object of the present invention is to provide a process for the recovery of BHT values, of the above mentioned character, which besides permitting efficient crystallization of realkylated BHT values, will produce a mother liquor suitable to be reused for further recovery of BHT values in admixture with the starting mother liquor.

A more particular object of the present invention is to provide a process for the recovery of BHT values, in accordance with the above, which will increase the concentration of said BHT values in order to obtain a high concentration of realkylatable material to be converted into fully crystallizable BHT.

The novel features that are considered characteristic of the present invention are set forth with particularity in the appended claims. The invention itself, however, both as to its organization and its method of operation, together with additional objects and advantages thereof, will best be understood from the following description of specific embodiments, which are to be considered as illustrative and not as limitative of the true spirit and scope of the invention.

DETAILED DESCRIPTION

In the prior art process for the obtention of BHT, p-cresol is reacted with isobutylene in the presence of an acid catalyst, preferably a mineral acid such as sulfuric or phosphoric acids, and at a temperature of from 50°C to 90°C, in order to obtain a reacted mixture containing high concentrations of BHT, and then crystallizing said reacted mixture, in order to precipitate the BHT which is generally obtained with a yield of from 75 to 80% of the theoretical yield, leaving a mother liquor of crystallization containing relatively high concentrations of BHT values in the form of residual p-cresol and mono-tert-butyl-p-cresol. The process for the obtention of BHT can be represented by means of the following equation:

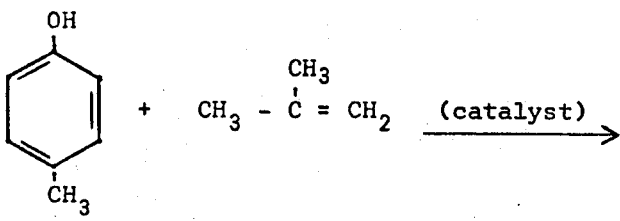 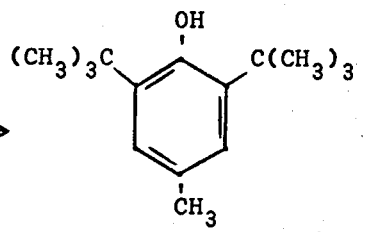

The 2,6-di-ter-butyl-p-cresol thus obtained, is generally accompanied, in the reacted mixture, by measurable proportions of certain side products, such as diisobutylene, mono-tert-butyl-p-cresol, lower polymers and higher polymers of cresol, as well as residual unreacted p-cresol.

Upon crystallization of the BHT, the residual mother liquors from said crystallization have a typical composition as follows:

| | |
|---|---|
| diisobutylene | 5–9% |
| p-cresol | 0.4–1% |
| mono-tert-butyl-p-cresol | 30–38% |
| 2,6-di-tert-butyl-p-cresol | 40–45% |
| lower cresol polymers | 15–18% |

If this mother liquor is distilled under vacuum, the objectionable crystallization inhibiting materials, namely, diisobutylene and cresol polymers are not removed therefrom, inasmuch as, while a considerable reduction in the concentration of diisobutylene is obtained by distillation, the concentration of cresol polymers is increased and some higher cresol polymers are formed, whereby if said mother liquor is distilled under vacuum in accordance with the prior art, a mixture of the following composition is obtained:

| | |
|---|---|
| diisobutylene | 1–2% |
| p-cresol | 1–1.5% |
| mono-tert-butyl-p-cresol | 35–40% |
| 2,6-di-tert-butyl-p-cresol | 38–42% |
| lower cresol polymers | 17–20% |
| higher cresol polymers | 0.5–1% |

From the above, it can be seen that, while the concentration of diisobutylene, which is highly objectionable to obtain proper crystallization of BHT upon realkylation, is considerably reduced, the same is not true of the cresol polymers, which concentration slightly increases and still more objectionable higher cresol polymers are formed during the distillation process, which prevent use of this distilled mother liquor in the realkylation of the BHT values in order to obtain a crystallizable reacted solution in accordance with the present invention.

In view of the above, in accordance with the process of the present invention, the crystallization mother liquor of a typical composition as per the above, is firstly subjected to a thermal cracking by heating the mother liquor to a temperature of around 200°C to 250°C, preferably 220°C, in the presence of a catalyst, preferably an acid catalyst and still more preferably a strong mineral acid such as sulfuric or phosphoric acids, whereby the cresol polymers are drastically cracked down into their components, thus considerably reducing the concentration of said polymers and at the same time considerably increasing the concentration of p-cresol which is produced by the cracking of said cresol polymers and also considerably increasing the concentration of mono-tert-butyl-p-cresol and also reducing the concentration of the residual 2,6-d-tert-butyl-p-cresol. A typical composition of the cracked mixture is as follows:

| | |
|---|---|
| diisobutylene | 16–20% |
| p-cresol | 9–12% |
| mono-tert-butyl-p-cresol | 46–50% |
| 2,6-di-tert-butyl-p-cresol | 20–23% |
| lower cresol polymers | 1–2% |
| higher cresol polymers | 0% |

The thus obtained cracked mixture is then steam distilled in order to drastically reduce the concentration of diisobutylene which is also highly objectionable for the proper and efficient crystallization of BHT. Upon steam distillation, a typical composition of the distilled mixture is as follows:

| | |
|---|---|
| diisobutylene | 1–2% |
| p-cresol | 15–20% |
| mono-tert-butyl-p-cresol | 50–58% |
| 2,6-di-tert-butyl-p-cresol | 20–25% |
| lower polymers of cresol | 2–3% |

From the above description of the typical composition of the steam distilled cracked mixture obtained in accordance with the process of the present invention, it can be seen that all the objectionable materials, which prevent efficient crystallization of the BHT from the reacted mixture, have been decreased in their concentrations down to a minimum which cannot be considered objectionable any more. Thus, the concentration of diisobutylene has been reduced to a value of from 1 to 2% by weight and the concentration of the lower polymers of cresol has been reduced down to 2 to 3% by weight, which cannot be considered as objectionable concentrations. It will also be noted that no higher cresol polymers are formed during the steam distillation process, whereby these highly objectionable materials do not exist in the reaction mixture obtained in accordance with the process of the present invention.

The above reaction mixture is then alkylated in strict accordance with the very well known BHT process, by the addition of suitable amounts of isobutylene, as well as the proper catalyst, in order to realkylate all the BHT values contained therein, namely, the monobutylated hydroxy toluene and the residual p-cresol which, in relatively large concentrations, are present in said reaction mixture obtained by the process of the present invention.

Upon realkylating the reaction mixture, a typical composition as follows is obtained:

| | |
|---|---|
| diisobutylene | 0–0.5% |
| p-cresol | 0.5–1% |
| mono-tert-butyl-p-cresol | 4–6% |
| 2,6-di-tert-butyl-p-cresol | 80–85% |
| lower cresol polymers | 8–12% |

The reactions which are effected during alkylation of the reaction mixture obtained in accordance with the process of the present invention, are represented by the following condensed equation:

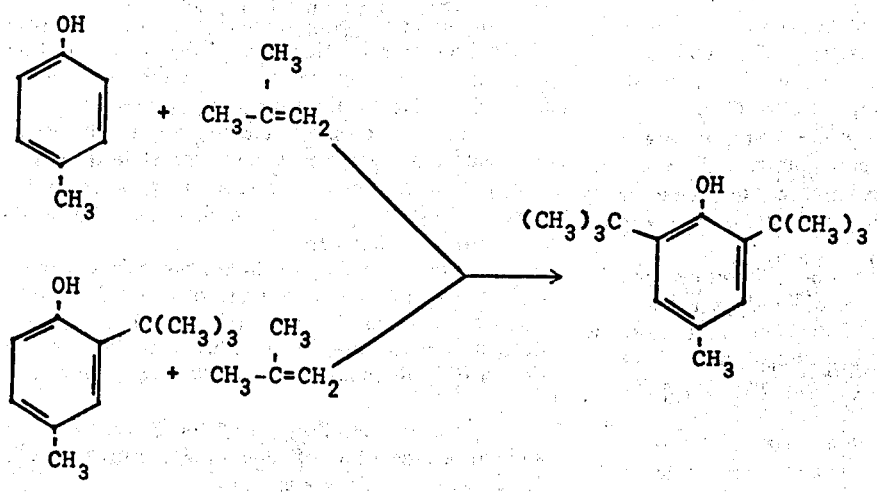

As relatively high concentrations of p-cresol and of mono-butylated hydroxy toluene exist in the reaction mixture obtained in accordance with the cracking and steam distillation process of the present invention, very good yields of 2,6-di-tert-butyl-p-cresol (BHT) are obtained which, upon crystallization of the reacted mixture, render an overall yield of from about 60 to 70% of BHT, with respect to the theoretical yield. This crystallization, on the other hand, produces residual mother liquors having a composition very similar to the composition of the starting mother liquor, whereby said residual mother liquors can be admixed with the stream of the starting mother liquor in order to be reused and retreated in the process of the present invention.

From the above, it can be seen that practically no BHT values are wasted, inasmuch as the residual mother liquors obtained upon realkylation and crystallization of the reaction mixture of the present invention are fully reused.

The present invention will be more clearly understood from the following illustrative examples.

EXAMPLE 1

56 grams (1 mole) of isobutylene were reacted with 104 grams (1 mole) of p-cresol in a suitable reactor, in the presence of a small amount of phosphoric acid and at a temperature of about 80°C. The reaction mixture was subjected to crystallization, in order to precipitate the thus formed 2,6-di-tert-butyl-p-cresol as a product. The mother liquors obtained from the crystallization step had an analysis as follows:

| | |
|---|---|
| diisobutylene | 7.81% |
| p-cresol | 0.41% |
| mono-tert-butyl-p-cresol | 34.32% |
| 2,6-di-tert-butyl-p-cresol | 41.22% |
| lower cresol polymers | 16.34% |

The above mother liquor was subjected to thermal cracking by heating the same to a temperature of about 220°C in the presence of a small amount of phosphoric acid, thereby causing a considerable cracking of the cresol polymers, and of the BHT itself, thus producing a cracked composition having the following analysis:

| | |
|---|---|
| diisobutylene | 18.67% |
| p-cresol | 10.36% |
| mono-tert-butyl-p-cresol | 48.08% |
| 2,6-di-tert-butyl-p-cresol | 21.47% |
| lower cresol polymers | 1.42% |

The thus obtained cracked composition was steam distilled, whereby a considerable reduction in the concentration of diisobutylene was obtained. The distillate showed the following analysis:

| | |
|---|---|
| diisobutylene | 1.82% |
| p-cresol | 17.6% |
| mono-tert-butyl-p-cresol | 54.6% |
| 2,6-di-tert-butyl-p-cresol | 23.1% |
| lower cresol polymers | 2.7% |

Approximately 1000 grams of the above described steam distilled reaction mixture was realkylated in a suitable reactor, by the addition of about 270 grams of isobutylene in the presence of a small amount of phosphoric acid and at a temperature of around 60°C, whereby practically all of the p-cresol in said mixture and around 90% of the mono-tert-butyl-p-cresol were realkylated to form additional 2,6-di-tert-butyl-p-cresol, thus producing a reacted mixture showing the following analysis:

| | |
|---|---|
| diisobutylene | 0.05% |
| p-cresol | 0.93% |
| mono-tert-butyl-p-cresol | 5.46% |
| 2,6-di-tert-butyl-p-cresol | 83.46% |
| lower cresol polymers | 10.1% |

The above reacted mixture was crystallized, with a recovery of around 62% by weight of the theoretical yield of 2,6-di-tert-butyl-p-cresol. A mother liquor showing an analysis very similar to the analysis of the starting mother liquor was obtained and said liquor was then admixed with the incoming starting mother liquor to reuse the same during a further cycle of operation.

The crystallization of the 2,6-di-tert-butyl-p-cresol was effected in a very efficient manner, and the product was easily crystallizable from this mixture due to the removal of the highly objectionable crystallization inhibiting compounds diisobutylene and cresol polymers down to a tolerable value.

EXAMPLE 2

The procedure of Example 1 was repeated by using a small amount of sulfuric acid instead of the phosphoric acid in all the catalyzed steps of the process, with the obtention of entirely similar results.

From the above it can be seen that a very economical, efficient and practical process has been provided for the recovery of BHT values from the mother liquors of the crystallization of BHT obtained by reacting p-cresol with isobutylene in the presence of an acid catalyst. The process of the present invention is capable of removing objectionable amounts of crystallization inhibiting compounds, namely, diisobutylene and lower and higher polymers of p-cresol extant in said mother liquors, whereby the thus treated mother liquors can be easily subjected to realkylation and crystallization with high yields of BHT.

The process of the present invention, therefore, renders a by-product previously considered as a waste product, reusable to produce additional amounts of BHT which were heretofore discarded in view of the impossibility of crystallizing said compound from the mother liquors obtained in the prior art BHT processes.

Although certain specific embodiments of the present invention have been shown and described, it is to be understood that many modifications thereof are possible. The invention, therefore, is not to be restricted except insofar as is necessitated by the prior art and by the spirit of the appended claims.

What is claimed is:

1. A process for the recovery of 2,6di-tert-butyl-p-cresol from a starting non-crystallizable mother liquor obtained from the crystallization of 2,6-di-tert-butyl-p-cresol produced by the alkylation of p-cresol with isobutylene, said starting non-crystallizable mother liquor comprising diisobutylene and lower and higher cresol polymers which inhibit crystallization of 2,6-di-tert-butyl-p-cresol, which comprises the steps of:
   a. thermally cracking said starting mother liquor at a temperature of from 200°C to 250°C, in the presence of an acid catalyst, in order to crack the lower and higher cresol polymers;
   b. steam distilling the cracked mixture to remove the diisobutylene in the presence of an acid catalyst;
   c. realkylating the cresols in the steam distilled reaction mixture by the addition of isobutylene; and
   d. crystallizing the thus formed additional 2,6-di-tert-butyl-p-cresol.

2. A process according to claim 1 wherein said starting mother liquor also contains mono-butylated hydroxy toluene which on being subjected to the realkylation step produces additional 2,6-di-tert-butyl-p-cresol.

3. A process according to claim 2 wherein said thermal cracking step is effected by heating said starting mother liquor to a temperature of 220°C in the presence of a catalytic amount of sulfuric acid.

4. A process according to claim 2 wherein said thermal cracking step is effected by heating said starting mother liquor to a temperature of 220°C in the presence of a catalytic amount of phosphoric acid.

5. A process according to claim 1 wherein the residual mother liquor obtained from the crystallization step d) upon realkylation of the reaction mixture, is admixed with incoming starting mother liquor to be reused in the cracking step.

6. A process according to claim 1 wherein said starting mother liquor is an admixture of about 5 to 9% of diisobutylene, about 0.4 to 1% of p-cresol, about 30 to 38% of monobutylated hydroxy toluene, about 40 to 45% of BHT and about 15 to 18% of lower cresol polymers.

7. A process according to claim 2 wherein said realkylation step c) is effected in the presence of a catalytic amount of a mineral acid.

8. A process according to claim 7 wherein said mineral acid is selected from sulfuric and phosphoric acids.

* * * * *